United States Patent [19]

Solladie et al.

[11] Patent Number: 5,047,575

[45] Date of Patent: Sep. 10, 1991

[54] NORBORNENE CARBOXYLIC ACIDS AND ESTERS

[75] Inventors: Guy Solladie, Strasbourg; Serge Forestier, Claye-Souilly; Gérard Lang, St-Gratien, all of France

[73] Assignee: L'Oreal, Paris, France

[21] Appl. No.: 258,132

[22] Filed: Oct. 14, 1988

[30] Foreign Application Priority Data

Oct. 16, 1987 [FR] France .................. 87 14298

[51] Int. Cl.$^5$ .................. C07C 69/74; C07C 35/20
[52] U.S. Cl. .................. 560/120; 562/510; 568/821; 568/827; 564/103; 549/398; 544/105; 556/482; 556/465
[58] Field of Search .................. 260/405.5, 405; 560/120; 562/502, 570; 568/821, 666, 823, 827; 549/398; 564/103; 544/105

[56] References Cited

U.S. PATENT DOCUMENTS 4,132,677 1/1979 Shaffer et al. .................. 514/772
4,267,111 5/1981 Willis et al. .................. 560/120

FOREIGN PATENT DOCUMENTS 0000719 2/1979 European Pat. Off. .
0001553 5/1979 European Pat. Off. .
0109910 8/1979 Japan .................. 260/405.5
2122200 1/1984 United Kingdom .

OTHER PUBLICATIONS

Chemical Abstracts, vol. 80, No. 23, Jun. 1974, p. 433, No. 132887f, Gream et al.

Primary Examiner—Jose G. Dees
Assistant Examiner—Deborah D. Carr
Attorney, Agent, or Firm—Cushman, Darby & Cushman

[57] ABSTRACT

Compounds, and a process for their preparation, have the formula

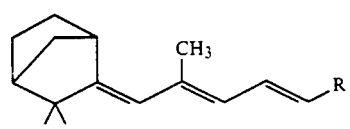

(I)

or corresponding salts thereof wherein R represents a group of the formula

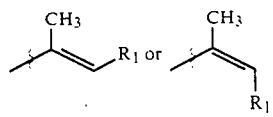

wherein $R_1$ represents oxazolinyl, $-C \equiv N$, $-CH_2OR_2$ or

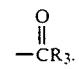

These compounds in the form of pharmaceutical or cosmetic compositions are useful for the treatment of keratinization disorders.

7 Claims, No Drawings

NORBORNENE CARBOXYLIC ACIDS AND ESTERS

The present invention relates to new norbornene derivatives, to their process of preparation and to their use in cosmetic, as well as, human and veterinary medicinal compositions.

The norbornene derivatives are compounds of the general formula

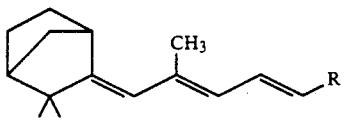
(I)

or corresponding salts thereof wherein R represents either a group of the formula:

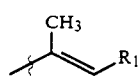
(II)

or a group of the formula

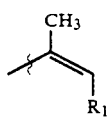
(III)

In the groups of formula II and III, $R_1$ represents a radical selected from the group consisting of oxazolinyl, $-C\triangledown N$, $-CH_2-O-R_2$,

wherein $R_2$ represents hydrogen, $C_1$-$C_6$ alkyl, cyclopentyl, cyclohexyl, tetrahydropyrannyl, $C_7$-$C_9$ aralkyl optionally substituted by one or more $C_1$-$C_6$ alkoxy groups, a radical of the formula

(IV)

wherein R', R" and R''', each independently, represent linear or branched $C_1$-$C_6$ alkyl, or aryl optionally substituted by a $C_1$-$C_4$ alkyl and $R_3$ represents hydrogen, $-OR_4$ or

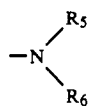

wherein $R_5$ and $R_6$, each independently, represent hydrogen, $C_1$-$C_6$ alkyl, or taken together form a $C_5$-$C_8$ heterocycle, and $R_4$ represents hydrogen or $C_1$-$C_6$ alkyl.

Representative, particularly preferred compounds of formula I according to the invention include those having the following structures:

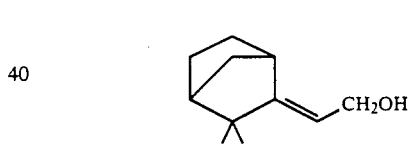
($I_A$)

($I_B$)

($I_C$)

($I_D$)

The compounds of formula I can be stereospecifically synthesized according to the nature of the substituent, R.

To obtain the compounds of formula I, the process of the present invention comprises (a) in a first step, oxidizing dl-patchenol of formula V

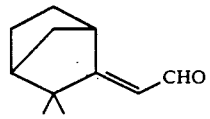
(V)

into dl-patchenal of formula VI (VI)

by activated $MnO_2$ in a solvent medium;

(b) in a second step, reacting the compound of formula VI with a solution of methylmagnesium iodide in a solvent medium and after having terminated the reaction, slowly oxidizing the solution by $MnO_2$ to obtain the compound of formula VII

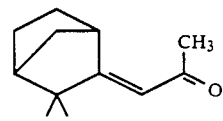
(VII)

(c) in a third step, preparing the organomagnesium compound, $HC\equiv C-MgBr$, in a solvent medium and reacting it, under a stream of acetylene, with the compound of formula VII to obtain the compound of formula VIII:

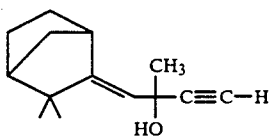
(VIII)

(d) in a fourth step, reacting in a solvent medium ethylmagnesium bromide with the compound of formula VIII, and then adding to the solution lower alkyl trans- or cis-formyl-3-butene-2-oate, according to whether a compound of formula I, wherein R represents a group of formula II or a group of formula III, respectively, is desired in order to obtain, respectively, a compound of formula IX or XVI:

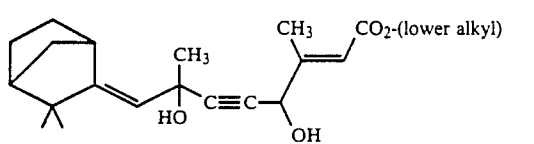
(IX)

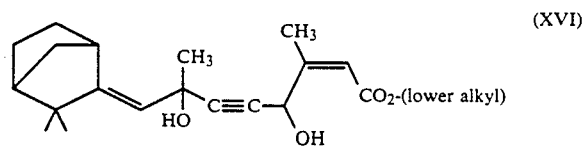
(XVI)

(e) in a fifth step, reacting in a solvent medium, the compound thus obtained with diisobutylaluminum hydride (DIBAL) to obtain the triol of formula X or XVII, respectively:

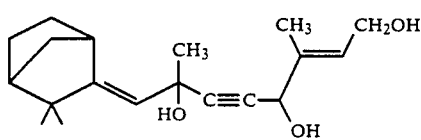
(X)

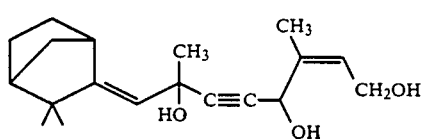
(XVII)

(f) in a sixth step, blocking the OH function at the end of the chain of the resulting triol by reacting said triol with a tri-(alkyl or aryl) silyl halide in the presence of imidazole to obtain the compound of formula XI or XVIII, respectively:

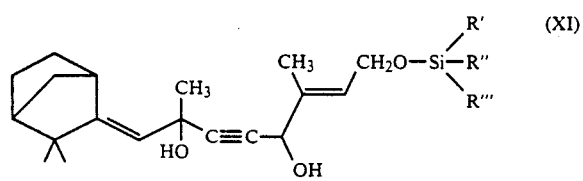
(XI)

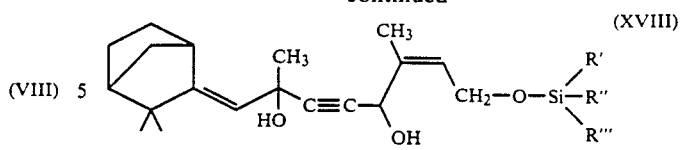
(XVIII)

wherein R', R'', and R''' have the meanings indicated above, reducing this latter compound in a solvent medium with hydrogen in the presence of a Pd/CaCo$_3$ catalyst deactivated with lead to obtain the diol of formula XII or XIX, respectively:

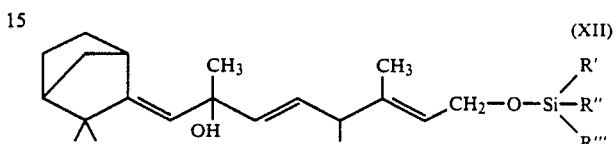
(XII)

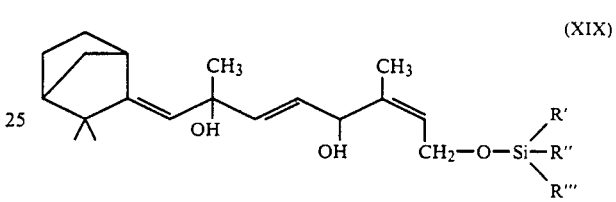
(XIX)

and then removing the two OH functions of the said diol by reacting said diol, in an anhydrous solvent medium, with a mixture (titanium trichloride and aluminum lithium hydride) to obtain the compound of formula XIII or XX, respectively:

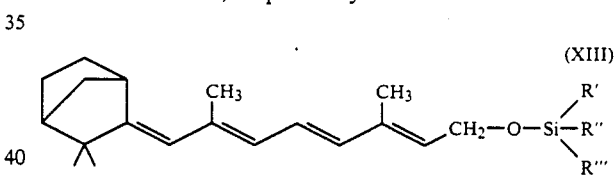
(XIII)

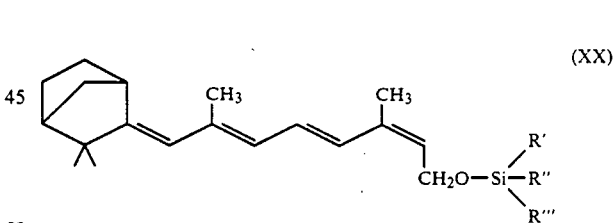
(XX)

and (g) in an optional seventh step, transforming this latter compound to obtain another compound of formula I where R is a group of formula II or III wherein R$_1$ is different from

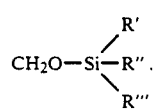

In a first embodiment of the present invention, for the preparation of a compound of formula I wherein R$_1$ is a CH$_2$OH radical, the end of the chain of the compound XIII or XX is unblocked by the action in a solvent medium of at least one fluoride so as to obtain the compound of formula XIV or XXI, respectively:

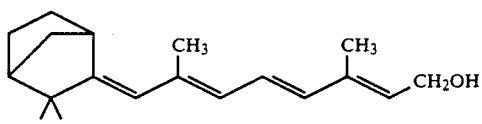

(XIV)

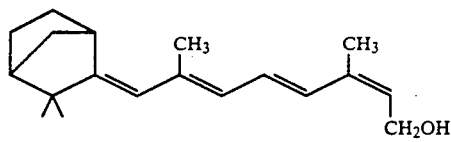

(XXI)

In a second embodiment of the present invention, for the preparation of a compound in which $R_1$ is a CHO radical, there is employed, as the initial reactant, the corresponding compound in which $R_1=CH_2OH$, which is prepared as indicated above, and this compound of formula XIV or XXI is oxidized in an anhydrous solvent medium by the action of $MnO_2$ so as to produce a compound of formula XV or XXII:

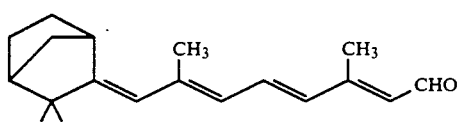

(XV)

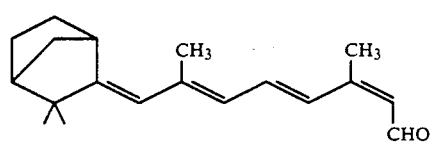

(XXII)

When it is desired to prepare a compound of formula I wherein $R_1$ is a $CO_2C_2H_5$ radical, there is employed as the initial reactant a corresponding compound in which $R_1$ is a CHO radical which is prepared as indicated above, and this compound is submitted, in the dissolved state in ethanol, to the action of an alkaline cyanide and silver oxide, AgO so as to obtain a compound of formula $I_A$ or $I_C$.

When it is desired to prepare a compound of formula I in which $R_1$ is a $CO_2H$ radical, there is employed, as an initial reactant, the corresponding product in which $R_1$ is a $CO_2C_2H_5$ radical, this product having been prepared as indicated above, and this ester is then submitted to the action of a hydroalcoholic solution of a strong base, after which the solution is adjusted to an acid pH. A compound of formula $I_B$ or $I_D$ is thus obtained.

These compounds are useful:

(1) in the treatment of dermatologic complaints related to a keratinization (differentiation-proliferation) disorder and principally for the treatment of acne vulgaris, comedons, polymorphs, cystic nodulo acne, secondary acne such as solar acne, medicamentous or occupational acne;

(2) in the treatment of other types of keratinization disorders and principally ichthyosis and ichthyosiform states, Darier's disease, palmo-plantar keratosis, leucoplasies and leucoplasiform states, and lichen;

(3) in the treatment of other dermatologic diseases linked to a keratinization disorder with an inflammatory and/or immunoallergic component, and principally all forms of psoriasis, be it cutaneous, mucous or ungual, and even rheumatoid psoriasis, or even cutaneous atophy, such as eczema, or respiratory atophy;

(4) in the treatment of all dermal or epidermal proliferations be they benign or malignant, be they of viral origin such as common warts, surface warts, and epidermodysplasie verruciforme, the proliferations being also able to be induced by ultra-violet radiations, principally in the case of basoepithelioma and cellular spino;

(5) in the treatment of other dermatologic disorders such as bullosa disorders and collagen disorders;

(6) in the treatment in the ophthalmologic field, principally for corneopathies; and (7) to combat ageing of the skin, in particular against the effects of the sun.

The compounds in accordance with the present invention exhibit good comedolytic activity in the test described by Bonne et al in the "International Journal of Cosmetic Science, 3, 23–28, 1981", this testing being carried out on the skin of the hairless rhino mouse, as recommended by Van Scott in 1972.

The present invention also relates to a new medicinal or pharmaceutical composition, intended principally for the treatment of the above-mentioned disorders, characterized by the fact that it comprises, in a pharmaceutically acceptable support, at least one compound of formula I or a corresponding salt thereof.

As the support for these compositions, any conventional support can be employed, the active compound being found either in the dissolved state or in the dispersed state in the said support.

The administration of these compositions can be effected enterally, parenterally, rectally, topically or occularly. The compounds of the invention are generally administered at a daily dosage of about 0.02 μg/kg to 2 mg/kg of body weight.

When administered enterally, the compositions of the present invention can be provided in the form of tablets, gelules, lozenges, syrups, suspensions, solutions, powders, granules or emulsions.

When administered parenterally, the compositions of the present invention can be provided in the form of solutions or suspensions for perfusion or injection.

When administered topically, the composition of the present invention can be provided in the form of ointments, tinctures, creams, salves, powders, patches, saturated pads, solutions, emulsions, lotions, gels, sprays or even suspension. These compositions can be either in anhydrous form or in aqueous form in accordance with clinical indications. Good activity of these compounds has been observed by topical administration over a very large range of dilution. There can be employed, principally, concentrations of the active product ranging from 0.0001 to 5 weight percent relative to the total weight of the composition. It is, however, possible to employ higher concentrations if necessary for a particular therapeutic application. However, the preferred concentrations of the active product are between 0.001 to 1 weight percent, based on the total weight of the composition.

When administered occularly, the compositions of the invention are provided, preferably, in the form of an eyewash.

The compounds of formula I are also found, in accordance with the present invention, useful in the cosmetic field, and in particular, in body hygiene and hair care compositions and principally for skin having acne tendencies, for the regrowth of the hair, to combat against hair loss, to combat against an oily appearance of the skin or hair, to prevent or treat the harmful effects of the sun or to treat physiologically dry skin.

The present invention thus relates to a cosmetic composition comprising, in a cosmetically acceptable support, at least one compound of formula I or a corresponding salt thereof. This cosmetic composition can be provided, principally, in the form of a lotion, gel, soap or shampoo.

The concentration of the compound of formula I in the cosmetic compositions of the present invention, ranges between 0.0001 and 2 weight percent and, preferably, between 0.001 and 1 weight percent, based on the total weight of the composition.

The medicinal and cosmetic compositions of the present invention can also contain inert or pharmacodynamically or cosmetically active additives, and principally: hydrating agents such as thiamorpholinone and its derivatives or urea; antiseborrheic agents, such as S-carboxymethylcysteine, S-benzylcysteamine and their derivatives, and tioxolone; anti-acne agents such as benzoyl peroxide; antibiotics such as erythromycin and its esters, neomycin, tetracyclines or 4,5-polymethylene-3-isothiazolinones; agents improving the growth of hair, such as "Minoxidil" (2,4-diamino-6-piperidino-3-pyrimidine oxide) and its derivatives, "Diazoxide" (3-chloromethyl-1,2,4-benzothiadiazine-1,1-dioxide) and "Phenytoin" (5,5-diphenyl-2,4-imidazolinedione) or oxapropanium iodide; anti-inflammatory agents, steroidal or non-steroidal; carotenoids and, principally, β-carotene; antipsoriasic agents such as anthralin and its derivatives and 5,8,11,14-eicosatetraynoic and 5,8,11-triynoic acids and their esters and amides.

The compositions according to the present invention can also contain flavor improving agents, preservatives, stabilizers, humidity regulating agents, pH regulating agents, osmotic pressure modifiers, emulsifiers, UV-A and UV-B filters, antioxidants such as α-tocopherol, butylhydroxyanisole or butylhydroxytoluene.

The following purely illustrative and non-limiting examples of preparing the active compounds of formula I, as well as several examples of compositions containing them, are given to illustrate the invention.

EXAMPLE 1

Preparation of the compound of formula XIII wherein R'=R"=CH$_3$ and R''' is tert. butyl, this compound having formula I where R is a group of formula II in which R$_1$—CH$_2$O—R$_2$ wherein R$_2$ is

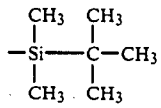

First step—preparation of the compound of formula VI:

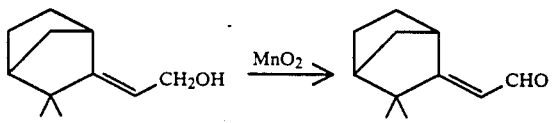

To a solution of 50 g (0.3 mole) of dl-patchenol in a liter of dichloromethane there are added, all at once, 10 equivalents of activated MnO$_2$ (prepared in accordance with the method described by. J. Attenburrow, J.Chem. Soc. 1952, 1104). The mixture is stirred at ambient temperature overnight and then filtered. The solvent is evaporated under reduced pressure thereby yielding 49 g of dl-patchenol.

Second step—preparation of the compound of formula VII:

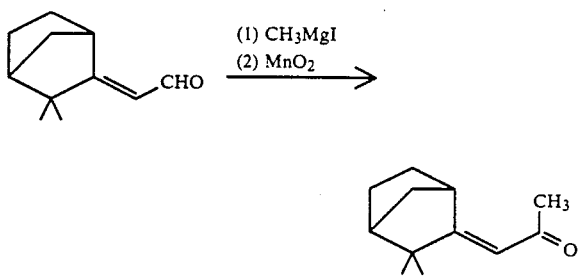

4 g (24.4 mmoles) of patechenal in solution in 50 cm$^3$ of anhydrous ether are slowly added to a solution of methylmagnesium iodide (1.5 eq. prepared starting with 5.2 g (36.6 mmoles) of methyl iodide and 0.9 g of magnesium in 50 cm$^3$ of ether). The reaction mixture is stirred for 15 minutes at ambient temperature and then poured into a cold saturated solution of ammonium chloride. The aqueous phase is extracted three times with ether. The organic phases are then washed with a saturated solution of sodium chloride and dried on magnesium sulfate. The ether solution is then rapidly filtered on silica and the filtrate is immediately oxidized with 10 equivalents of MnO$_2$. The reaction mixture is stirred for three days at ambient temperature, then filtered and the solvent is distilled under reduced pressure. 3.7 g of the expected product (yield=85%) are obtained which is used without further purification in the third step.

Third step—preparation of the compound of formula VIII:

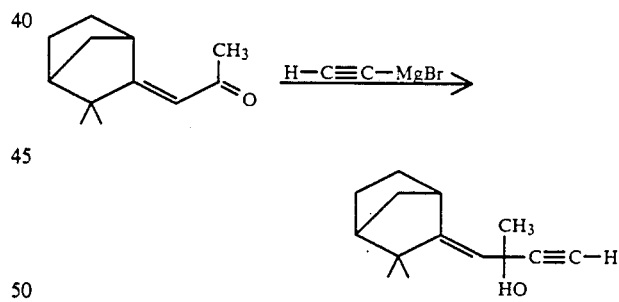

A stream of acetylene is slowly introduced into 400 cm$^3$ of anhydrous tetrahydrofuran, cooled to −40° C., for 1 hour. The cooling bath is withdrawn and a solution of ethylmagnesium bromide (prepared starting with 0.2 mole, 21.8 g of ethyl bromide, 4.9 g of magnesium and 100 cm$^3$ of anhydrous tetrahydrofuran) is rapidly added to the acetylene solution while maintaining the temperature below 35° C. After the addition, the reaction mixture is stirred for 30 minutes at ambient temperature. There are then slowly added 23.2 g (0.13 mole) of the compound, obtained in the course of the second step, in solution in 100 cm$^3$ of tetrahydrofuran. Stirring is continued for one hour. The stream of acetylene, which had been maintained up to then, is discontinued and the reaction mixture is poured into a saturated ammonium chloride solution. The aqueous phase is extracted twice with ether. The organic phases are washed with a saturated solution of sodium chloride, dried on magnesium sulfate and the solvent is distilled under reduced pressure.

The resulting product is purified by silica gel chromatography by using as the solvent a 95/5 mixture (by volume) of hexane and ethyl acetate. 23.9 g (yield =90%) of the expected product are obtained.

Fourth step—preparation of the compound of formula IX:

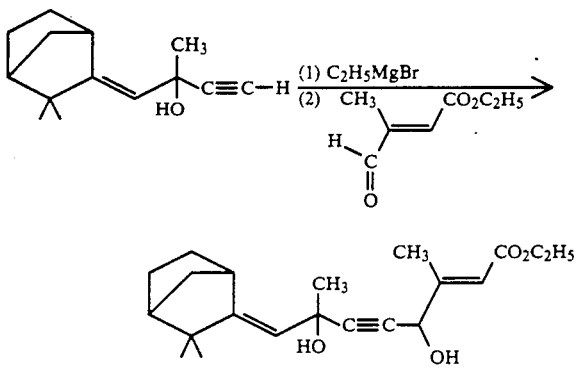

The compound obtained in the course of the third step (1.3 9 or 6.36 mmoles) is added to a solution of ethylmagnesium bromide (13.4 mmoles) in 40 cm³ of tetrahydrofuran. The reaction mixture is stirred for 1 hour, and there is then added 0.9 g (6.36 mmoles) of ethyl trans formyl-3-buten-2-oate. After 15 minutes, the mixture is poured into an equivalent amount of saturated ammonium chloride. After extraction with ether, the organic phases are dried on sodium sulfate, and the solvent is distilled under reduced pressure.

The product is purified by chromatography on silica gel by using as the solvent a 30/70 mixture (by volume) of ethyl acetate and hexane.

The expected product is obtained with a yield of 75%.

Fifth step—preparation of the compound of formula X:

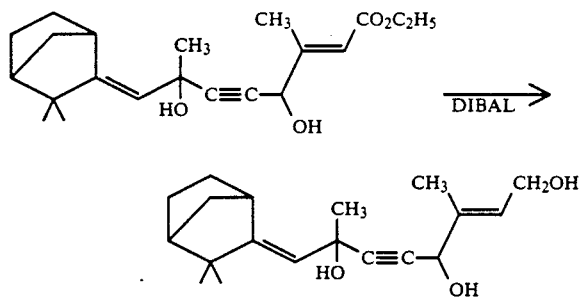

A solution of 1.4 g (4.3 mmoles) of the compound, obtained in the fourth step, in 100 cm³ of anhydrous tetrahydrofuran cooled to −20° C. There are then rapidly added 11.5 cm³ of a 1.5M solution of diisobutylaluminum hydride (DIBAL) (17.2 mmoles). Ten minutes after the end of the addition, a saturated solution of ammonium chloride is added and then a 20% solution of HCl so as to dissolve the formed precipitate. After separation of the phases, the aqueous phase is extracted twice with ether. The organic phases are washed with a saturated solution of sodium chloride, dried on sodium sulfate and the solvent is distilled under reduced pressure.

The expected product is obtained with a yield of 90%. It is used without further purification for the following step.

Sixth step—preparation of the compound of formula XIII:

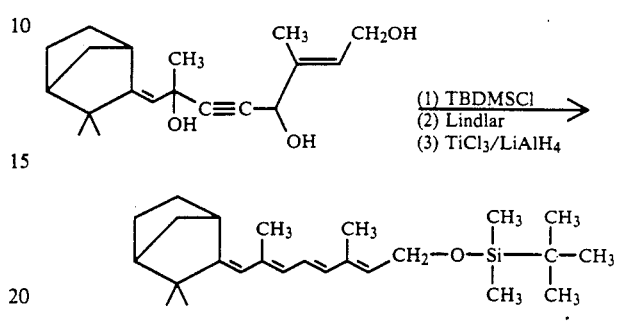

(a) preparation of the compound of formula XI

To 3.02 g of the triol obtained in the course of the fifth step, in 150 cm³ of dimethylformamide, there are added one equivalent (1.5 g) of tert. butyl-dimethyl silyl chloride and 2 equivalents (1.36 g) of imidazole. The solution is stirred for 6 hours at ambient temperature, and then diluted with one liter of water. The product is extracted with ether (3 times - 120 cm³). The ether phases are washed with a saturated solution of ammonium chloride. After drying on magnesium sulfate and distillation of the solvent under reduced pressure, the expected product is obtained in the form of an oil, which is employed without further purification in the following step.

(b) preparation of the compound of formula XII:

0.42 g of the compound obtained above is dissolved in 20 cm³ of absolute methanol. After addition of 0.8 g of Lindlar catalyst (Pd/CaCO₃ deactivated with lead), the air contained in the reactor is removed and replaced by hydrogen. The suspension is then vigorously stirred for 72 hours and the reaction is followed by thin layer silica chromatography using an 80/20 (by volume) mixture of ethylacetate/hexane as the eluant.

The catalyst is filtered and the solvent is evaporated. The product thus obtained is used without purification in the following step.

(c) preparation of the compound of formula XIII:

Two equivalents (1.43 g) of TiCl₃ are weighed in a round bottom flask, previously oven dried. 30 cm³ of anhydrous tetrahydrofuran are added and one equivalent of LiAlH₄ dosed in solution in ether (0.176 g) is introduced under argon.

The mixture is then stirred for 10 minutes at ambient temperature and 0.8 equivalent (1.56 g) of the diol obtained above in solution in 20 cm³ of tetrahydrofuran is added. After one hour at ambient temperature, the reaction mixture is treated with 10 cm³ of water and 60 cm³ of 0.1N HCl.

The phases are separated and the aqueous phase is extracted twice with 30 cm³ of ether. The organic phases are washed with 60 cm³ of a saturated solution of sodium chloride and then dried on magnesium sulfate. The solvent is distilled under reduced pressure. 1.30 g of the product of formula XIII are obtained.

EXAMPLE 2

Preparation of the compound of formula XIV constituting a compound of formula I where R is a group of formula II wherein $R_1=CH_2OR_2$ wherein $R_2=H$ 1 g of the compound obtained in Example 1 is dissolved in 15 cm³ of a mixture of tetrahydrofuran and acetonitrile containing ⅓ by volume of tetrahydrofuran. The solution thus obtained is treated with 5 equivalents of anhydrous sodium fluoride and 0.1 equivalent of perfectly pure pyridinium fluoride which has been crushed into fine particles just before use. The reaction is carried out in the absence of light, under argon, after having added to the solution 2 g of 4 Å molecular sieve.

After 5 hours of stirring at ambient temperature, the reaction mixture is treated with 10 cm³ of a saturated solution of ammonium chloride and 10 cm³ of water. After decanting, the aqueous phase is extracted twice with 10 cm³ of ether. The organic phases are combined and washed with 20 cm³ of a saturated solution of sodium chloride. After drying on sodium sulfate, the solvent is distilled under reduced pressure at ambient temperature. 0.60 g of the product of formula XIV is obtained.

EXAMPLE 3

Preparation of the compound of formula XV constituting a compound of formula I where R is a group of formula II wherein

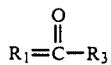

wherein $R_3=H$ 1 g of the compound obtained at the end of Example 2 (without additional purification) is dissolved in 15 cm³ of anhydrous carbontetrachloride in the absence of light. There are added, with vigorous stirring, 1.5 g (5 equivalents) of freshly prepared $MnO_2$. After 30 minutes of stirring at ambient temperature, the suspension is rapidly filtered on silica gel, and the solvent is distilled at ambient temperature under reduced pressure. 0.90 g of the product of formula XV is obtained.

EXAMPLE 4

Preparation of the compound for formula $I_A$ 1 g of the compound obtained at the end of Example 3 (without additional purification) is dissolved in 15 cm³ of ethanol. There are successively added 5 equivalents of sodium cyanide (0.86 g) and 6 equivalents of AgO (2.6 g). The suspension thus obtained is stirred at 40° C. in the absence of light for 14 hours. The reaction mixture is filtered and the solution is chromatographed on silica gel (eluant - ethyl acetate/hexane containing 5 volume percent of ethyl acetate).

After evaporation of the solvent under reduced pressure, the expected product is obtained and has the following NMR (nuclear magnetic resonance properties): NMR ¹H spectrum in solution in CDCl₃:

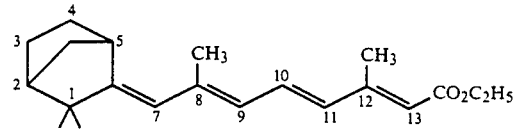

$\delta = 1.05-1.06$ ppm (2s, 6H, 2 CH₃ in 1)
$\delta = 1.24-1.74$ ppm (m 6H, CH₂ of the ring)
$\delta = 1.29$ ppm (t, 3H, J=7Hz, CH₃ of the ethyl group)
$\delta = 1.90$ ppm (s large, 1H, H in 2)
$\delta = 2.04$ ppm (s, 3H, CH₃ in 8)
$\delta = 2.35$ ppm (s, 3H, CH₃ in 12)
$\delta = 3.31$ ppm (s large, 1H, H in 5)
$\delta = 4.16$ ppm (q, 2H, J=7Hz, CH₂ of the ethyl group)
$\delta = 5.61$ ppm (s, 1H, H in 13)
$\delta = 5.75$ ppm (s, 1H, H in 7)
$\delta = 6.08$ ppm (d, 1H, J=11Hz, H in 9)
$\delta = 6.21$ ppm (d, 1H, J=15Hz, H in 11)
$\delta = 6.93$ ppm (dd, 1H, J=11Hz and 15 Hz, H in 10)

EXAMPLE 5

Preparation of the compound of formula $I_B$ 0.5 g of the ester obtained in Example 4 is suspended in 25 cm³ of ethanol and 25 cm³ of 6M aqueous solution of soda. The suspension is stirred at 50° C. in the absence of light, until complete dissolution.

The reaction mixture is then diluted with 500 cm³ of water and the ethanol is distilled under reduced pressure. The aqueous phase is acidified to pH 3 by the addition of a 10 weight percent aqueous solution of HCl. It is then extracted 3 times with 50 cm³ of ether. The organic phase is dried on sodium sulfate and the solvent is distilled under reduced pressure. The expected product is obtained after recrystallization in methanol. This product has the following characteristics:

Melting point - 173°-175° C.; NMR ¹H spectrum in solution in CDCl₃:

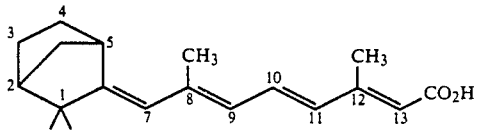

$\delta = 1.05-1.06$ ppm (2s, 6H, 2 CH₃ in 1)
$\delta = 1.22-1.93$ ppm (m 7H, CH₂ of the ring and H in 2)
$\delta = 2.03$ ppm (s, 3H, CH₃ in 8)
$\delta = 2.36$ ppm (s, 3H, CH₃ in 12)
$\delta = 3.32$ ppm (s large, 1H, H in 5)
$\delta = 5.61$ ppm (s, 1H, H in 13)
$\delta = 5.78$ ppm (s, 1H, H in 7)
$\delta = 6.15$ ppm (d, 1H, J=11Hz, H in 9)
$\delta = 6.26$ ppm (d, 1H, J=16 Hz, H in 11)
$\delta = 6.98$ ppm (dd, 1H, J=11Hz and 16Hz, H in 10)

EXAMPLE 6

Preparation of the compound of formula XX wherein R'=R"=R'"=C$_2$H$_5$, this compound corresponding to formula I is a group of formula III wherein R$_1$=CH$_2$—O-R$_2$ wherein R$_2$ is

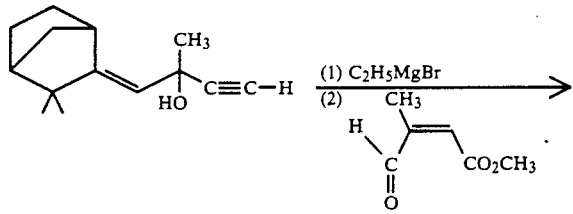

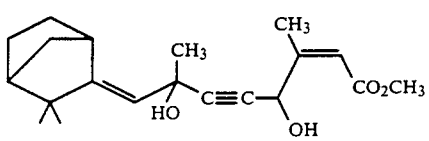

The first three steps of Example 1 are identically reproduced.

4th step: preparation of the compound of formula XVI

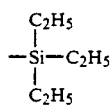

This compound is obtained in accordance with the operating procedures described in the 4th step of Example 1 except that the ethyl trans-formyl-3-butene-2-oate is replaced by methyl cis-formyl-3-butene-2-oate.

The expected product is obtained with a yield of 70% after chromatography on silica gel using as the eluant a mixture of ethyl acetate and hexane (30/70 by volume).

5th step: preparation of the compounds of formula XVII:

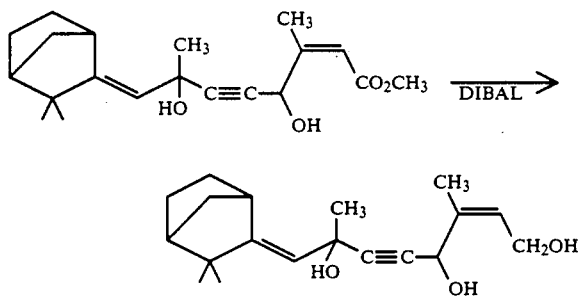

This compound is obtained in accordance with the operating procedures described in the 5th step of Example 1 by using the 12-cis isomer obtained in accordance with the preceding step.

6th step: preparation of compound of formula XX:

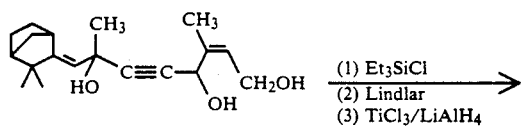

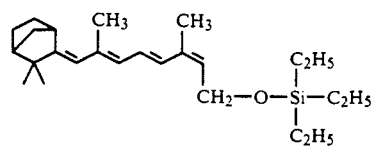

(a) preparation of the compound of the formula

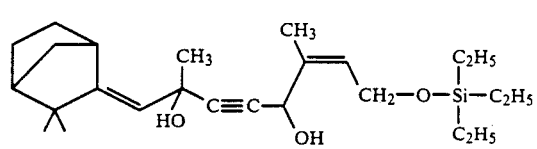

This compound is obtained in accordance with the operating procedures described in the first stage of the 6th step of Example 1. The tert. butyldimethylsilyl chloride is replaced by triethylsilyl chloride and the 12-trans triol is replaced by the 12-cis triol obtained at the end of the 5th step of Example 6.

(b) preparation of the compound of formula XX:

This compound is obtained in accordance with the operating procedures described in the 2nd and 3rd stages of the 6th step of Example 1: the 12-trans isomer is replaced by the 12-cis isomer in each stage.

EXAMPLE 7

Preparation of a compound of formula XXI constituting a compound of formula I where R is a group of formula III wherein R$_1$=CH$_2$OR$_2$ wherein R$_2$=H This compound is obtained in accordance with the operating procedures described in Example 2 by using the product of formula XX obtained in Example 6 rather than the product obtained at the end of Example 1.

EXAMPLE 8

Preparation of a compound of formula XXII constituting a compound of formula I where R is a group of formula III wherein

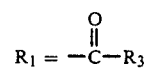

wherein R$_3$=H

This compound is obtained in accordance with the operating procedures described in Example 3 by replacing the 12-trans isomer with the 12-cis isomer obtained at the end of Example 7.

EXAMPLE 9

Preparation of the compound of formula IC

This compound is obtained in accordance with the operating procedures described in Example 4 by replacing the 12-trans isomer with the 12-cis isomer obtained in Example 8.

After chromatography on silica gel using as the eluant a mixture of ethyl acetate and hexane, containing 5% of ethyl acetate, the expected product is obtained having the following NMR characteristics:

NMR $^1$H spectrum in solution in CDCl$_3$:

[Structure: bicyclic group with =CH-C(CH₃)=CH-CH=CH-C(CH₃)=CH-CO₂C₂H₅ chain, numbered 1-13]

δ=1.05-1.06 ppm (2s, 6H, 2 CH₃ in 1)
δ=1.26-1.76 ppm (m 6H, CH₂ of the ring)
δ=1.29 ppm (T, 3H, CH₃ of the ethyl group J=7Hz)
δ=1.91 ppm (s large, 1H, H in 2)
δ=2.03 ppm (s, 3H, CH₃ in 8)
δ=3.30 ppm (s large, 1H, H in 5)
δ=4.17 ppm (q, 2H, J=7Hz, CH₂ of the ethyl group)
δ=5.61 ppm (s, 2H, H in 13 and H in 7)
δ=6.18 ppm (d, 1H, J=11Hz, H in 9)
δ=6.92 ppm (dd, 1H, J=11 and 15Hz, H in 10)
δ=7.72 ppm (d, 1H, J=15Hz, H in 11)

EXAMPLE 10

Preparation of the compound of formula $I_D$:

[Structure: bicyclic group with =CH-C(CH₃)=CH-CH=CH-C(CH₃)=CH-CO₂H chain]

This product is obtained in accordance with the operating procedures described in Example 5; the 12-trans isomer is replaced by the 12-cis isomer obtained in Example 9. After recrystallization in ether, then in methanol, the expected product is obtained and has the following characteristics:

NMR ¹H spectrum in solution in CDCl₃:

[Structure: bicyclic group numbered 1-5 with chain numbered 7-13 ending in CO₂H, with CH₃ at positions 8 and 12]

δ=1.05-1.06 ppm (2s, 6H, 2 CH₃ in 1)
δ=1.18-1.76 ppm (m 6H, CH₂ of the ring)
δ=1.91 ppm (peak large, 1H, H in 2)
δ=2.05 ppm (s, 3H, CH₃ in 8)
δ=2.09 ppm (s, 3H, CH₃ in 12)
δ=3.22 ppm (peak large, 1H, H in 5)
δ=5.64 ppm (s, 2H, H in 13 and H in 7)
δ=6.21 ppm (d, 1H, J=11, 5Hz, H in 9)
δ=6.96 ppm (dd, 1H, J=11, 5 and 15Hz, H in 10)
δ=7.70 ppm (d, 1H, J=15Hz, H in 11)
Melting point: 181°–183° C. (decomposition)

EXAMPLE 11

A gel is prepared by producing the following formulation:
Compound of formula $I_B$:0.050 g
Erythromycin base:4.000 g
Butylhydroxy toluene:0.050 g
Hydroxypropylcellulose, sold by Hercules under the trade name "KLUCEL HF":2.000 g
Ethanol (95%), sufficient amount for:100.000 g This gel is applied to skin exhibiting dermatosis or to acne skin, 1 to 3 times each day. After 6 to 12 weeks of treatment at an application rate of 2 to 10 mg/cm² of skin being treated, a significant improvement is observed.

EXAMPLE 12

The following formulation intended to be packaged in a gelule is prepared:
Compound of formula $I_A$:0.060 g
Cornstarch:0.060 g
Lactose, sufficient amount for:0.300 g
The gelules employed are made of gelatin, titanium oxide and a preservative.

There are administered to an adult person 1 to 3 gelules each day for the treatment of psoriasis. After 30 days of treatment at a per day rate of 1 mg/kg of body weight of the treated subject, a significant improvement is observed.

EXAMPLE 13

An antiseborrheic lotion is prepared by admixing the following components:
Compound of formula $I_B$:0.030 g
Propylene glycol:5.000 g
Butylhydroxytoluene:0.100 g
Ethanol, sufficient amount for:100.000 g This lotion is applied twice each day to a seborrheic scalp. After 2 to 6 weeks of treatment at an application rate of to 4 mg per cm² of treated scalp, a significant improvement is observed.

EXAMPLE 14

A gel for topical application is prepared by admixing the following components:
Compound of formula $I_B$:0.05 g
Ethanol:43.00 g
α-tocopherol:0.05 g
Cross-linked polyacrylic acid, sold by Goodrich under the trade name "CARBOPOL 940":0.50 g
Triethanolamine (20% aqueous solution):3.80 g
Water:9.30 g
Propylene glycol, sufficient amount for:100.00 g This gel is applied twice each day to acne skin. After 6 to weeks of treatment at an application rate of 2 to 10 mg/cm² of skin being treated, a significant improvement is observed.

EXAMPLE 15

A nonsoluble tablet is prepared by admixing the following substances:
Compound of formula $I_D$:0.025 g
Lactose:0.082 g
Stearic acid:0.003 g
Purified talc:0.015 g
Sweetening agent, sufficient amount
Colorant, sufficient amount
Rice starch, sufficient amount for:0.500 g Three tablets are orally administered each day to an individual suffering from psoriasis. After 30 days of treatment at a daily rate of 1 mg/kg of body weight of the subject being treated, a significant improvement is observed.

EXAMPLE 16

A solution is prepared by producing the following formulation:
Compound of formula $I_C$:0.20 g Polyethylene glycol (M.W.=400):80.00 g
Ethanol (95°), sufficient amount for:100.00 g This solution is applied to acne skin 3 times each day. After 6 to 12 weeks of treatment at an application rate of 1 to 4 mg/cm² of skin being treated, a significant improvement is observed.

EXAMPLE 17

A capillary lotion to combat hair loss and to improve hair growth is prepared by admixing the following components:

Propylene glycol:20.00 g
Ethanol:34.92 g
Polyethylene glycol (M.W.=400):40.00 g
Water:4.00 g
Butylhydroxy anisole:0.01 g
Butylhydroxy toluene:0 02 g
Compound of formula $I_B$:0.05 g
2,4-diamino-6-piperidino-3-pyrimidine oxide:1.00 g This lotion is applied twice each day to a scalp having been subjected to significant hair loss. After 3 months of treatment at a rate of 1 ml per application, a significant improvement is observed.

EXAMPLE 18

A two-part anti-acne kit is prepared as follows:
(a) A gel having the following formulation is prepared:

Ethyl alcohol:48.40 g
Propylene glycol:50.00 g
Cross-linked polyacrylic acid, sold by Goodrich under the trade name "CARBOPOL 940":1.00 g
Butylhydroxy anisole:0.05 g
Butylhydroxy toluene:0.05 g
α-tocopherol:0.10 g
Compound of formula $I_B$:0.10 g (b) A gel having the following formulation is prepared:

Ethyl alcohol:5.00 g
Propylene glycol:5.00 g
Disodium salt of EDTA:0.05 g
Cross-linked polyacrylic acid, sold by Goodrich under the trade name "CARBOPOL 940":1.00 g
Triethanolamine (99%):1.00 g
Sodium lauryl sulfate:0.10 g
Purified water:75.05 g
Benzoyl peroxide hydrated to 25%:12.00 g The mixture of the two gels is made extemporaneously, weight for weight, at the moment of use.

This mixture is applied twice each day to acne skin. After to 6 weeks of treatment at an application rate of 2 to 10 mg/cm² of skin being treated, a significant improvement is observed.

What is claimed is:

1. A compound having the formula

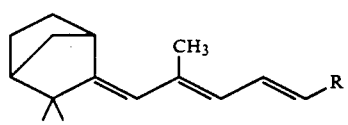

(I)

or a corresponding salt thereof, wherein
R represents

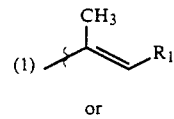

(II)

or

(III)

wherein
$R_1$ represents a radical selected from the group consisting of oxazolinyl, —C≡N, —CH₂—O—$R_2$ and

$R_2$ represents hydrogen, $C_1$-$C_6$ alkyl, cyclopentyl, cyclohexyl, tetrahydropyrannyl, $C_7$-$C_9$ aralkyl unsubstituted or substituted with one or more $C_1$-$C_6$ alkoxy groups, a radical of the formula

wherein R', R" and R''' each independently, represents linear or branched $C_1$-$C_6$ alkyl or aryl unsubstituted or substituted by $C_1$-$C_4$ alkyl,
$R_3$ represents hydrogen, —OR₄
wherein R₄ represents hydrogen or $C_1$-$C_6$ alkyl.

2. A compound having the formula

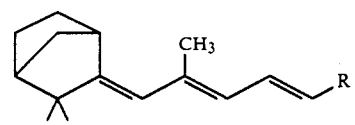

(I)

or a corresponding salt thereof, wherein
R represents

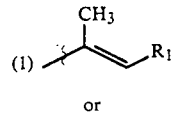

(II)

or

(III)

wherein
$R_1$ represents

and
$R_3$ represents —OR₄
wherein R₄ represents hydrogen or $C_1$-$C_6$ alkyl.

3. The compound of claim 2 having the formula

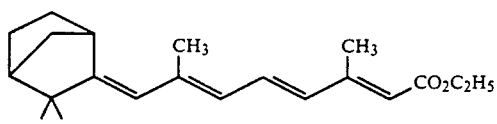 (I$_A$)
4. The compound of claim 2 having the formula
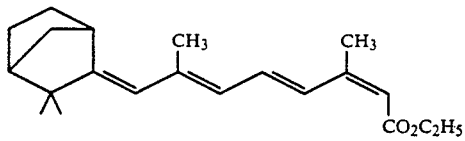 (I$_C$)
5. A compound having the formula
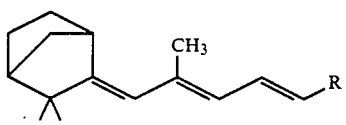 (I)
or a corresponding salt thereof, wherein
R represents
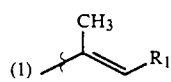 (II)
or
-continued
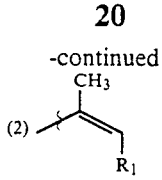 (III)
wherein
R$_1$ represents
and
R$_3$ represents —OR$_4$ wherein R$_4$ represents hydrogen.
6. The compound of claim 5 having the formula
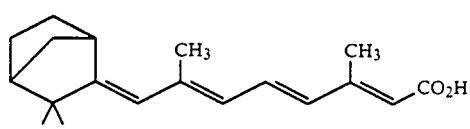 (I$_B$)
7. The compound of claim 5 having the formula
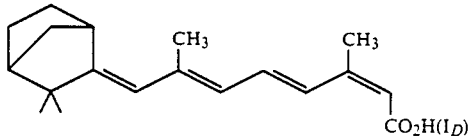 (I$_D$)
* * * * *